United States Patent [19]

Thirumalachar et al.

[11] 4,415,662

[45] Nov. 15, 1983

[54] MICROBIAL DEGRADATION OF PETROLEUM MATERIALS

[76] Inventors: Mandayam J. Thirumalachar; Mandayam J. Narasimhan, Jr., both of P.O. Box 506, Locust St., Walnut Creek, Calif. 94596

[21] Appl. No.: 288,615

[22] Filed: Jul. 30, 1981

[51] Int. Cl.$^3$ .................. C12N 11/14; C12N 1/26; C12N 1/14; C10G 32/00
[52] U.S. Cl. ................................ 435/176; 435/195; 435/248; 435/254; 435/281; 435/911
[58] Field of Search ............ 435/248, 281, 911, 183, 435/188, 195, 174, 176, 254

[56] References Cited

U.S. PATENT DOCUMENTS

| | | | |
|---|---|---|---|
| 3,769,164 | 10/1973 | Azarowicz | 435/281 |
| 3,843,517 | 10/1974 | McKinney et al. | 435/281 X |
| 3,870,599 | 3/1975 | Azarowicz | 435/281 |
| 3,871,956 | 3/1975 | Azarowicz | 435/281 |
| 3,871,957 | 3/1975 | Mohan et al. | 435/281 |
| 4,284,509 | 8/1981 | Lindörfer et al. | 435/281 X |

*Primary Examiner*—David M. Naff
*Attorney, Agent, or Firm*—Neuman, Williams, Anderson & Olson

[57] ABSTRACT

Crude petroleum and petroleum products such as encountered in land or sea-borne spills are degradated by contact with the microorganism, *Actinomucor elegans* (Ediam) Benj. and Hasselt, Strain No. TC-405, ATCC 20613, or an enzymatic active material obtained therefrom. The microorganism and enzymatic active material may be used in combination with a carrier and/or detergent. The microorganism and enzymatic active material are effective for degradation in inhospitable climates and various land and open water conditions, generate no deleterious products or chemicals, and are long-acting and rapid in onset of initial activity.

60 Claims, No Drawings

MICROBIAL DEGRADATION OF PETROLEUM MATERIALS

BACKGROUND OF THE INVENTION

1. Field of Invention

The invention relates to the degradation of the hydrocarbon constituents of crude petroleum and petroleum products in any environment. It particularly relates to the degradation by emulsification, solubilization and break down of said petroleum materials by application of an effective amount of *Actinomucor elegans* or its enzymatic active principles.

2. Description of the Prior Art

There has been considerable effort expended in attempts to develop mechanical, chemical and microbiological processes for cleaning up oil leaks, spills and slicks on the world's land mass, oceans and seaways, which have become a common, virtually daily-occurring problem caused by sinking or damaged ships and broken oil pipelines. An additional extensive and related effort has been made to avoid and rectify oil pollution resulting from the cleaning of the tanks of oil tankers, bilges and fuel bunkers after the unloading of oil cargo or emptying of fuel stores. The pollution caused by the cleaning of petroleum storage tanks on tankers is particularly substantial, as several thousand gallons of crude petroleum may remain on the interior sides of the tanks after unloading of the cargo, which eventually forms a highly viscous, gel-like mass over time if the tanks are not cleaned. This mandates that the tanks be cleaned frequently, which results in the production of thousands of gallons of oil/water/cleaning compound for each vessel, which may initially be held in a slop tank, but eventually is dumped into the open water. While the cleaning compound normally constitutes one or a combination of the known biodegradable detergent compounds or compositions, there still is a substantial fouling problem and pollution from the petroleum material even though not aggravated by detergent pollution.

The seriousness of open sea oil pollution is known both from practical experience and from the pollution studies of Milz & Frazer, *Jour. Petr. Techn.* 24:255–262 (1972). Milz and Frazer found that an oil slick of 40 gallons of crude oil would cover a 200×30 foot area 10 minutes after being spilled into the open sea, which slick would expand to an area 100 feet wide and one-half mile long after one hour.

Despite this work and the vast literature reporting it, the art still lacks an efficient yet simple solution to the problem of cleaning up spills of crude petroleum and petroleum products. Known methods are cumbersome and of unknown efficacy in a given situation. Stein et al. German Patent No. 2547742 discloses a typical system, in which polymers are used to absorb crude petroleum in an oil slick, where the oil must be then removed by skimming of the spill-polluted water environment.

Particular emphasis has been placed in this area on the development of a microbial agent which demonstrates hydrocarbon degradation or consumptive properties, which properties essentially comprise the ability to emulsify, solubilize, break down and consume the deleterious petroleum materials. The normally water-soluble components of crude petroleum constitute only about 0.02% by weight of the material; it is known that bacteria capable of degrading hydrocarbons utilize them only in dissolved states. Hence most of the hydrocarbons present in crude petroleum, which are highly water insoluble, cannot be broken down by known microbial degradation techniques.

Experimental studies using crude petroleum as a microbial substrate have heretofore been carried out which have, however, led to the discovery of microbes having hydrocarbon degrading properties, as well as an affinity to the substrate, under laboratory conditions. Ludvik et al., *Experientia* 24:255 (1958), described a hydrocarbon-degrading yeast having cell components which made them adhere to oil droplets. Korowitz et al., *J. Appl. Microbiology* 30:10–19 (1975), disclosed strain UP-2, and showed the importance of the relationship of the size of the oil droplet to the growth of the microbe, that size being regulated by the emulsifying characteristics of the microbe while growing on the hydrocarbons. Iguchi et al., *Agri Biol. Chem.* 33:1657–58 (1969), showed that *Candida petrophilium*, which degraded hydrocarbons, produced an emulsifying agent composed of peptides and fatty acid moieties. Similar work with Arthrobacter, Brevibactorium and Nocardia species found that a trehalose-lipid was produced in the oil phase. Gholsen et al., U.S. Nat. Tech. *Int. Serv.* AD Rep. No. 757071 (1973), stated that, while a procedure to chemically modify enzymes in order to cause them to adhere to a hydrocarbon-water interface without appreciable loss of activity had been effective to some extent in a lysozome, RN-ase and 2 lipases, it was left to the future to provide microorganisms which would by production of extracellular emulsifying enzymes biodegrade hydrocarbons in oil spills.

The production by the known laboratory-effective microorganisms of emulsifying agents and subsequent droplet formation appears to enhance pseudosolubilization of the hydrocarbons and the uptake of those hydrocarbons into cells. Scott et al., *J. Bacteriol.* 127:469–480 (1976) showed that, with cells of Acinetobacter sp., the uptake of solid phase hydrocarbons was by pseudosolubilization. It is probable that the organism had evolved surface active substances which acted as wetting agents and as detergents.

The art has long discussed the potential advantages of artificially seeding polluted areas with pure or mixed cultures of microorganisms which are known to degrade the hydrocarbon constituents of crude petroleum and petroleum products. Efficacy demonstrated by experimental or industrial fermentor work using hydrocarbons, however, rarely has but the slightest relationship to what happens in the open sea or other large water or land environment. The regulated temperature and pH conditions, with optimum nutrition, aeration and agitation, of the fermentor or experimental set-up is totally absent in the natural environment or the sea. The art has also found such seeding to be impractical with the few known hydrocarbon-degrading microorganisms due to the impossibility of providing the nitrogenous and phosphoric nutrition necessary to sustain the microbes in such vast, open environments.

Solution of the nutritional problem by attempts to induce the oil degradation microbes to fix atmospheric nitrogen by recombinant techniques using bacterium-carrying plasmids for nitrogen fixation has been carried out (Gutnik et al. *Ann, Rev. Appl. Microb.* 370–396 (1977)), but has demonstrated no present success.

In sum, the art totally lacks any effective method, compound or composition capable of degrading crude petroleum and petroleum products in actual, non-laboratory conditions and environments, such as open ocean spills of crude petroleum. The art particularly lacks any such degradative method, compound or composition utilizing a microorganism such as a bacterium or fungus having such actual environment effectiveness.

There is a need in the art, then, for a method, compound and composition capable of effecting the degradation of crude petroleum and petroleum products in an environment, particularly a salt water environment, such as would be encountered in land or sea-borne spills of crude petroleum or petroleum products. There is a particular need for a microorganism-based method, compound and composition which demonstrates the capability of degrading and breaking down by emulsification, solubilization and ingestion of the hydrocarbon constituents of crude petroleum and petroleum products large quantities of such materials in any environment, including the catastrophic spill of crude petroleum which occurs in the sinking of an ocean-going tanker vessel and in the blowing out of an oil pipeline. There is a further need for a method, compound and composition which may be utilized to clean the interior of vessel tanks, particularly those of oil tankers used to transport crude petroleum and petroleum products. Particularly needed is a method, compound and composition which may be utilized in conjunction with the known biodegradable detergent compounds and compositions which the art now uses to carry out such cleaning.

The optimum combination of properties for a method, compound and composition for effecting the degradation of crude petroleum and petroleum products in an environment particularly one based in the utilization of a microorganism, is such that:

(1) the method, compound and composition must demonstrate acceptable efficacy in actual, non-laboratory environments, including inhospitable climates and various land and open water—salt water/ocean conditions, yet be in such form as to itself be non-toxic and non-deleterious, and to generate no deleterious products or chemicals harmful to or befouling of said environment;

(2) the method, compound and composition must be longacting and rapid in the onset of its initial activity, and require no further support or sustaining activities after initiation and/or application to the crude petroleum or petroleum product;

(3) the method, compound and composition must be self-sustaining, so as to require no additional provision for nutrients or other supporting chemicals or compositions other than what the crude petroleum or petroleum products provide;

(4) the method, compound and composition, together with the degraded, solubilized crude petroleum or petroleum products, must be self-dissipating, so as to require no retrieval and disposal of any petroleum-laden component or material;

(5) the method, compound and composition must be easy to effect and manufacture, while safe to personnel applying the composition or carrying out the process at all stages and times of its preparation and use; and (6) the method, compound and composition must be compatible with and capable of use in conjunction with known biodegradable detergent compounds and compositions.

None of the microorganism-based laboratory degradative processes or compositions known to the art, however, and particularly none of the actual environment methods or compositions (of which there are none which are microorganism based), provide this optimum combination of properties desirable with respect to the degradation of crude petroleum and petroleum products.

SUMMARY OF THE INVENTION

The present invention relates to a method, compound and compositions for effecting the degradation of crude petroleum and petroleum products in any environment. The method comprises the application to the crude petroleum and petroleum products in an environment of an effective amount of the fungus *Actinomucor elegans* (Ediam) Benj. and Hasselt., Strain No. TC-405, its enzymatic active principle compound, a broth comprising it, or a carrier medium comprising the fungus or its enzymatic active principle compound.

The compound and compositions of the present invention comprise the fungus *Actinomucor elegans* (Ediam) Benj. and Hasselt., Strain No. TC-405 (which term herein comprises generically its cultural derivatives and mutants) and a biologically pure culture of the fungus *Actinomucor elegans* (Ediam) Benj. and Hasselt., Strain No. TC-405 having the identifying characteristics of ATCC 20613, which fungus, cultural derivatives, mutants and culture are capable of effecting degradation of crude petroleum and petroleum products in an environment. An enzymatic active principle compound which degrades, by emulsification, solubilization and break down, the hydrocarbon constituents of petroleum materials, and which is produced by and isolated from the *Actinomucor elegans* fungus, is also provided by the present invention, as are compositions comprising the fungus or the enzymatic active principle compound produced by the fungus and a carrier medium.

The method, compound and compositions of the invention are particularly efficacious when utilized to degrade crude petroleum and petroleum products in a salt water environment, including the open ocean. The method, compound and compositions of the invention are also particularly efficacious when utilized to clean petroleum storage tanks on oil tankers, either alone or in combination with known, biodegradable and compatible detergent compounds and compositions.

The present invention overcomes the lackings and drawbacks of the prior art by providing a method, compound and composition for effecting degradation of crude petroleum and petroleum products which demonstrates efficacy in actual, non-laboratory environments, including inhospitable climates and various land and open water conditions, yet is non-toxic and non-deleterious, generates no deleterious products or chemicals, is long-acting and rapid in the onset of its initial activity, does not require further support or sustenance after application to the crude petroleum or petroleum product, is, together, with the degraded, solubilized crude petroleum or petroleum products, self-dissipating, so as to require no retrieval and disposal of any petroleum-laden component or material, is easy and safe to manufacture and utilize, and is compatible with and capable of use in conjunction with known biodegradable detergent compounds and compositions.

Accordingly, it is an object of this invention to provide a method of effecting the degradation of crude petroleum and petroleum products which is effective in actual, non-laboratory environments, including inhospitable climates and various land and open water conditions, yet is easy and safe to carry out.

It is a further object of this invention to provide compounds and compositions which degrade crude petroleum and petroleum products which are non-toxic and non-deleterious, and which do not generate or cause the generation of deleterious products or chemicals.

It is yet another object of this invention to provide compounds and compositions which degrade crude petroleum and petroleum products having a long activity and rapid initial onset of that activity, but which require no further support or sustenance after application to said petroleum material.

It is a further object of this invention to provide methods, compounds and compositions for degrading crude petroleum and petroleum products wherein the degraded, solubilized petroleum and degrading compound or composition are self-dissipating after the substantial completion of the degradation of the hydrocarbon constituents of the petroleum material, so as to require no retrieval from the environment and disposal of any petroleum-laden component.

Finally, it is an object of this invention to provide methods, compounds and compositions for degrading crude petroleum and petroleum products which are compatible with and capable of use in conjunction with known biodegradable detergent compounds and compositions.

Other objects and advantages of this invention will become apparent upon reading the following detailed description and appended claims.

DESCRIPTION OF THE PREFERRED EMBODIMENT

The preferred method of the invention provides for the degradation of crude petroleum and petroleum products in an environment. The method comprises contacting said petroleum material with an effective amount of a strain of a fungus, *Actinomucor elegans* (Ediam) Benj. & Hasselt., Strain No. TC-405, isolated from the soil.

The fungus strain, *Actinomucor elegans* (Ediam) Benj. & Hasselt., Strain No. TC-405, has been deposited in accordance with the provisions of MPEP §608.01(p) (1981), and may be obtained from the permanent colleciton of the American Type Culture Collection, Rockville, Md., where it has been deposited under an unrestricted deposit as *Actinomucor elegans* ATCC 20613.

An "effective amount" of the strain of the fungus *Actinomucor elegans* (Ediam) Benj. & Hasselt., Strain No. TC-405, is an amount sufficient to degrade, by emulsification, solubilization, break down and consumption, the quantity of crude petroleum or petroleum products present in the environment which it is desired to degrade or remove.

The fungus strain *Actinomucor elegans* (Ediam) Benj. & Hasselt., Strain No. TC-405, was isolated from soil from a group of mucoraceous fungi and bred to a pure form of superior efficacy with respect to hydrocarbon degradation by strain selection techniques, known to the art, which extended over several generations. This involved the utilization of standard techniques in growing daughter generations and selecting single cell colonies which were then grown in known fermentation media to measure the capacity of those cultures to degrade petroleum incorporated into said media. This also provided superior, enhanced mixing properties in the *Actinomucor elegans* with respect to crude petroleum or petroleum products, allowing ready mixing with the petroleum hydrocarbon and emulsification and consumption thereof in the process of further growth of the fungus.

The superior properties of the biologically selected strain of *Actinomucor elegans* (Ediam) Benj. & Hasselt., Strain No. TC-405, are reflected in the aforesaid culture deposited with and having the identifying characteristics of ATCC 20613.

The fungus strain of *Actinomucor elegans* (Ediam) Benj. & Hasselt., Strain No. TC-405, grows, when inoculated on agar, as colonies which are white at first, with radiating white coenocytic mycelium. The colonies soon turn greyish, with the development of erect sporangiophores bearing globose sporangia and dark spores in large numbers. Identification of the strain was based on the morphology of the fruiting structures and spore measurements.

The biomass generated by *Actinomucor elegans* (Ediam) Benj. & Hasselt., Strain No. TC-405, in liquid nutrient media, compared to that generated by other microorganisms such as bacteria, is at least several times greater per unit time. This rapid growth and biomass-generating capacity of the *Actinomucor elegans* fungus provides it with capabilities to maintain itself and its degradation of hydrocarbon constitutents of petroleum materials in all types of environments, including open ocean, over time, and to continue its growth activity and rapid metabolization of said hydrocarbon constituents.

The *Actinomucor elegans* fungus grows readily on most of the known media used for culturing fungi under laboratory conditions, including solid agar media such as potato dextrose agar, Sabaouraud's agar, corn meal agar, glucose-peptone agar, and glucose-yeast-peptone agar.

The fungus may be grown in submerged culture on a variety of the known media, and is capable of utilizing various carbon sources, such as alcohols, fatty acids from oils, sugars and polysaccharides, and nitrogen sources, both organic and inorganic in nature. The addition of various amino acids and vitamins, as is known in the antibiotic and drug arts, has an effect of the growth of *Actinomucor elegans* and its production of enzymatic active principle compounds, which comprises its hydrocarbon emulsifying and break down constituent agent. Boosting of the pseudosolubilization properties of the fungus to achieve breakdown of the petroleum material may be provided by addition of these known amino acids, vitamins, and growth-promoting substances.

The preferred method of the invention involves utilization of the *Actinomucor elegans* fungus in any form and level of biological strength or purity for degradation of petroleum materials. A particularly preferred method of the invention utilizes the biologically pure form, produced by the aforementioned strain selection techniques, of the strain of *Actinomucor elegans* (Ediam) Benj. & Hasselt., Strain No. TC-405, for contacting with the crude petroleum or petroleum product in an environment to cause degradation.

The environment in which the method of the invention demonstrates efficacy comprises any land or water area, enclosed or open, including salt water bodies and open ocean locations. No loss of efficacy results from petroleum presence in fresh rather than salt water, or vice versa. These environments also include man-made localities and objects, such as the inside of closed or open storage tanks and vessels, particularly oil storage tanks in oil tanker vessels, the interior of reaction vessels, chemical processing apparatus and piping, the interior portions of internal combustion engines and related fuel storage tanks or sumps, and the interior of pipelines and related pumping equipment. The environments in which the method of the invention is efficacious includes virtually any locality in which the *Actinomucor elegans* fungus or its enzymatic active principle compounds can be introduced. This would also comprise underground oil formations or other naturally occurring oil formations.

The method of the invention may be effected in parallel or concert with, or otherwise concurrently or as a part of other known industrial and chemical processes compatible therewith. These processes would include those not destructive of the *Actinomucor elegans* fungus, such as secondary degradation of undesired petroleum products after an initial separatory or extractive procedure.

Another preferred embodiment of the method of the invention for effecting degradation of crude petroleum and petroleum products in an environment comprises the application to said petroleum material of an effective amount of a composition comprising the strain of *Actinomucor elegans* (Ediam) Benj. & Hasselt., Strain No. TC-405, fungus and a carrier medium. The carrier medium comprises any of the standard commercially available carrier media. Particularly preferred carrier mediums are particulate porcelain clay, bentonite clay, and sodium carbonate, alone or in combination. Especially preferred carrier mediums are combinations of porcelain clay or bentonite clay with sodium carbonate, wherein the sodium carbonate may most preferably comprise about 50% by weight.

A further preferred embodiment of the method of the invention comprises the application of an effective amount of *Actinomucor elegans* and a carrier medium to crude petroleum or petroleum products in an environment, followed by further addition of a fungi culture medium to said petroleum material after application of the fungus. Fungi culture media useful in this embodiment are again well known in the antibiotic and drug arts, and may include those used for culturing fungi in the laboratory, such as potato dextrose agar or Sabaouraud's agar. A preferred media for such post-fungus application addition is particulate wheat bran. Other media, including micronized cereal, micronized corn cob, vegetable waste products (such as cereal husks), hay, seaweed powder and mixtures thereof, may also be utilized.

Yet another preferred embodiment of the method of the invention comprises the addition of a compatible biodegradable detergent compound or composition to the composition comprising the *Actinomucor elegans* fungus and carrier medium prior to application to the petroleum material. The presence of the detergent aids in release and dispersion of the enzymatic active principle compound(s) when the composition is applied to petroleum material in a water environment, or when a water solution if made up to effect cleansing of the oil-laden surfaces of oil tanker oil storage compartments.

Another preferred embodiment of the method of the invention comprises a variant on direct contact of the *Actinomucor elegans* fungus per se with the crude petroleum or petroleum product. Degradation of the petroleum materials in this additional embodiment is effected by growing the strain of *Actinomucor elegans* (Ediam) Benj. & Hasselt., Strain No. TC-405, in a liquid fungi culture medium, separating and filtering the resulting broth, adjusting the pH of the filtrate to about 4 to 4.5, adding a carrier medium to the filtrate to adsorb the enzymatic active principle compound produced by the fungi, agitating the carrier medium-filtrate mixture, separating and recovering the carrier medium from said mixture, and applying an effective amount of said active principle-bearing carrier medium to said petroleum material. The growth may be carried out by those procedures of fermentation and growth well known to the art for the production of antibiotics and enzymes, such as the procedure described in U.S. Pat. No. 4,082,613, issued Apr. 4, 1978, at column 6, line 18 et seq., which description is specifically incorporated herein and made a part hereof. Again, the carrier medium may comprise any of the carrier media known in the drug and pharmaceutical arts effective to adsorb the enzymatic active principles produced by the fungus. Particularly preferred media are particulate porcelain clay, bentonite clay, and sodium carbonate, alone or in combination. Especially preferred carrier mediums are combinations of porcelain clay or bentonite clay and sodium carbonate, wherein the sodium carbonate may most preferably comprise about 50% by weight. The carrier material may be added to the filtrate in a proportion of from about 6 to about 10 grams per liter of filtrate.

A variation of this preferred embodiment comprises the addition of the particulate sodium carbonate after the other carrier material constituents are recovered from the filtrate. Again, preferably about 50% by weight of the final composition should comprise sodium carbonate, the remainder being made up of the clay bearing the *Actinomucor elegans* enzymatic active principle compound. The sodium carbonate addition may be followed by grinding of the resulting combination to produce a homogeneous mass. The ground combination may further be air dried under vacuum to produce a dry, powdery mass or dry particulate mass, depending on the degree of grinding practiced.

In this embodiment, it is advantageous to grow said *Actinomucor elegans* in a nutrient media in aerated, agitated fermentors. Particularly preferred nutrients, which may be present singly or in combination with themselves and other known fungi culture media and media constituents, include corn starch, glucose, particulate wheat bran, cotton seed hydrolysate, such as PROFLO TM, manufactured by Traders Oil Mill Co., P.O. Box 1837, Fort Worth, Tex. 76101, mineral salts and other carbon-nitrogen source materials. It is also desirable, particularly where a salt-water environment will be encountered by the fungus, to include in said fungi culture medium salt water, either in the form of natural sea water or as a solution of sodium chloride, alone or with other electrolytes present in natural sea water. A small quantity of a lubricating oil or light petroleum oil may also be added as an enzyme-production inducer.

The carrier medium containing the *Actinomucor elegans* enzymatic active principle compound may be applied to the petroleum materials in the environment in any effective manner. A preferred method of applying the material in large-scale applications comprises dusting from an airplane or helicopter, or broadcasting from apparatus or vehicle, such as a boat.

The invention also provides a preferred method for preparing a compound for effecting degradation of petroleum materials in an environment. The method comprises growing the strain of *Actinomucor elegans*

(Ediam) Benj. & Hasselt., Strain No. TC-405, in a liquid fungi culture medium to produce a broth, harvesting the resulting broth, and isolating from said broth an enzymatic active principle compound or compounds. It is particularly preferred to utilize the biologically pure *Actinomucor elegans* culture having the characteristics of ATCC 20613. The active principle compound can be separated from the broth by techniques well known in the antibiotic, drug and enzyme arts, including absorption, elution and precipitation techniques, and may thereafter be concentrated or reduced to a dry form by well-known methods familiar to those arts.

A particularly preferred method for preparing a composition for effecting degradation of crude petroleum and petroleum products in an environment comprises growing *Actinomucor elegans* (Ediam) Benj. & Hasselt., Strain No. TC-405, in a liquid fungi culture medium, separating and filtering the resulting broth, adjusting the pH of the filtrate to about 4 to 4.5, adding a carrier medium (as hereinbefore described) to said filtrate to adsorb the enzymatic active principle compound produced by the fungi, agitating the carrier medium-filtrate composition, and separating and recovering the active principle-bearing carrier medium composition from said mixture.

The enzymatic active principle compound or carrier medium-containing composition may be isolated by air drying said broth under vacuum, for example, which results in the recovery of a dry active principle material.

A variation of this preferred embodiment comprises the addition of the particulate sodium carbonate after the other carrier material constituents are recovered from the filtrate. Again, preferably about 50% by weight of the final composition should comprise sodium carbonate, the remainder being made up of the clay bearing the *Actinomucor elegans* enzymatic active principle compound. The sodium carbonate addition may be followed by grinding of the resulting combination to produce a homogeneous mass. The ground combination may further be aired dried under vacuum to produce a dry, powdery mass or dry particulate mass, depending on the degree of grinding practiced.

In these enzymatic compound and composition production methods, it is again advantageous and preferred to grow said *Actinomucor elegans* fungus in aerated and agitated fermentors in a media which contains certain nutrients. Particularly preferred nutrients, which may be present singly or in combination with themselves and other known fungi culture media and media constituents, include glucose, particulate wheat bran, cotton seed hydrolysate, such as PROFLO ™, manufactured by Traders Oil Mill Co., P.O. Box 1837, Fort Worth, Tex. 76101, mineral salts and other carbon-nitrogen source materials. It is also desirable to include in said fungi culture medium salt water, either in the form of natural sea water or as a solution of sodium chloride, alone or with other electrolytes in natural sea water. A particularly preferred fungi culture medium for use in this method contains glucose, cotton seed hydrolysate and salt water, and an optimum culture further contains particulate wheat bran in addition to said glucose, cotton seed hydrolysate and salt water.

The preferred compounds and compositions of the invention for effecting degradation of crude petroleum and petroleum products comprise the enzymatic active principle compound or compounds produced by the strain of *Actinomucor elegans* (Ediam) Benj. & Hasselt., Strain No. TC-405, the fungus itself, the biologically pure culture of the fungus, and a composition comprising any of said compounds and a carrier medium, including compositions comprising a biodegradable detergent compound or composition.

The enzymatic active principle compound of the invention is produced by the method of the invention herein-before described. The compound, which may be recovered as a dry material, constitutes the enzyme(s) produced by *Actinomucor elegans* (Ediam) Benj. & Hasselt., Strain No. TC-405, which effects the degradation of the hydrocarbon constituents of the crude petroleum and petroleum products by emulsification, solubilization or pseudosolubilization and break-down. It is non-toxic and non-deleterious to the environment, and leads to no formation of toxic or deleterious products during or after hydrocarbon degradation.

The biologically pure culture of the invention is that culture of the strain of *Actinomucor elegans* (Ediam) Benj. & Hasselt., Strain No. TC-405, resulting from the application of the known serial strain technique to the fungus as isolated from the soil over several generations, said culture having the characteristics of ATCC 20613 and being capable of optimum effecting of degradation of crude petroleum and petroleum products in an environment.

The preferred compositions of the invention comprise the combination of the enzymatic active principle compound produced by the *Actinomucor elegans* fungus, the *Actinomucor elegans* fungus, or the biologically pure culture of the fungus with a carrier medium, including compositions comprising a biodegradable detergent compound or composition. The carrier media heretofore set forth are suitable for combination with said fungi or compounds to produce the compositions.

A particularly preferred composition of the invention, which demonstrates particular efficacy in the cleaning of oil storage tanks in oil tankers, comprises any of the previously described enzymatic active principle-bearing carrier medium compositions in combination with a compatible biodegradable detergent compound or composition, which detergent is preferably added to said composition in an amount of about 1 to 5 volumes of said detergent per volume of composition.

The mechanism by which the compositions of the invention effect degradation of crude petroleum and petroleum products is not completely understood. Without wishing to be bound by this explanation, it appears that the unique enzyme compound or compounds produced by the strain of *Actinomucor elegans* (Ediam) Benj. & Hasselt., Strain No. TC-405, causes an emulsification and solubilization or pseudosolubilization, due to its surface active properties, of the hydrocarbon constituents of the petroleum materials. Once so solubilized, the fungus then breaks down the hydrocarbon constituents and utilizes the breakdown products as a growth media or nutrient, resulting in the metabolization of the petroleum material.

The result is a biomass of non-toxic, non-deleterious fungus, or fungus plus carrier medium, left in the environment, either on the surface of a land area, on the surface of a body of water, or located in an artificial environment such as the interior of an oil storage tank. If exposed to the elements and general weather cycles, the fungus biomass, once deprived of a further source of sustenance on completion of the hydrocarbon constituent break down and degradation of the petroleum material, is itself rapidly degraded and absorbed into the environment, with no toxic or deleterious effects. If the biomass is in an enclosed artificial environment, it need only be removed and placed in a settling tank, dump area or otherwise exposed to the elements and general weather cycle to effect its degradation in turn.

Degradation of the crude petroleum and petroleum products is therefore effected by the methods, compounds and compositions of this invention, without concomitant production of further toxic or deleterious substances serving to further foul the environment which is sought to be cleansed.

The following examples illustrate the invention:

EXAMPLE 1

A liquid fungi culture medium containing 1% by weight cotton seed hydrolysate (PROFLO ™, manufactured by Trader's Corporation), 2% corn starch by weight, the balance being salt water (0.5% sodium chloride by weight), was sterilized by autoclaving for 30 minutes at 15 lbs. steam pressure. The sterilized medium was then cooled, and thereafter 100 cc of medium in a 500 cc Erlenmeyer flask was seeded with 5 cc of a spore suspension inoculum of *Actinomucor elegans* (Ediam) Benj. & Hasselt., Strain No. TC-405, taken from a 10-day old culture on potato dextrose agar. Incubation/fermentation of the fungus was carried out by placing the seeded flask on a rotary shaker (220 rpm) at 28° C. Growth was complete at the end of 72 to 84 hours.

A 500 cc Erlenmeyer flask was filled with 100 cc of sea water to which 10 cc of petroleum hydrocarbon (lubricant oil) was added. The oil spread over the water and adhered to the sides of the flask when shaken.

To the oil/water combination was added 3 cc of the *Actinomucor elegans* broth, and the flask was shaken. The lubricant oil adhering to the sides of the flask immediately sloughed off, and the sides of the flask became clean. The oil/fungus mass thereafter first turned to a heap of rounded oil balls with a whitish, frothy structure. With continued shaking, the oil disintegrated into small droplets. Control flasks without the *Actinomucor elegans* broth showed no change despite continued shaking.

The fungal mycelium floated on the surface, in contact with the oily phase, though some mycelium physically sank to the bottom also. On standing for more than 15 days, the mycelium proved to be alive and continued to grow, showing a lack of a need for nitrogenous sources for maintenance growth.

EXAMPLE 2

(a) A liquid fungi culture medium containing 1% by weight cotton seed hydrolysate (PROFLO ™, manufactured by Trader's Corporation), 2% glucose by weight, the balance being salt water (0.5% sodium chloride by weight), was sterilized by autoclaving for 30 minutes at 15 lbs. steam pressure. The sterilized medium was then cooled, and thereafter 100 cc of medium in a 500 cc Erlenmeyer flask was seeded with 5 cc of a spore suspension inoculum of *Actinomucor elegans* (Ediam) Benj. % Hasselt. taken from a 10-day old culture on potato dextrose agar. Incubation/fermentation of the fungus was carried out by placing the seeded flask on a rotating shaker (220 rpm), at 28° C. Growth was complete at the end of 72 to 84 hours.

(b) The broth resulting from part (a) hereof was filtered and the pH of the filtrate was adjusted to between about 4 to 4.5 with mineral acid (sulfuric acid). A porcelain clay, known also as 'bolus alba' ($Al_2O_2.2H_2O$—$SiO_2$) was then added to the filtrate in a proportion of from about 6 to 10 grams of clay per liter of filtrate. The porcelain clay/filtrate combination was then agitated well to obtain complete adsorption of the enzymatic active principle compound(s) produced by the *Actinomucor elegans* fungus. The mixture was then filtered and the porcelain clay bearing the absorbed active principle compound(s) removed for later use.

(c) The procedure in part (b) was repeated, except that bentonite clay was substituted in place of the porcelain clay, and the pH of the filtrate was adjusted to about 4.

(d) The still-wet porcelain clay of part (b) and bentonite clay of part (c) were also mixed with an equal volume by weight of particulate sodium carbonate and ground well. The sodium carbonate, due to the moisture present in the respective clays, mixed well. The materials (porcelain clay/sodium carbonate, bentonite clay/sodium carbonate) were thereafter dried under vacuum to a friable powder in which form they could be stored until required for use.

(e) The still-wet porcelain clay of part (b) and bentonite clay of part (c) were also formulated by adding a well-known liquid washing detergent (Crystal White ™, manufactured by Colgate-Palmolive Company) in a proportion of about 1 to 5 volumes of the detergent for each volume of the wet clay. The mixture was then homogenized and stored until required for use.

(f) The still-wet porcelain clay/sodium carbonate and bentonite clay/sodium carbonate compositions of part (d) were also formulated by adding a well-known liquid washing detergent (Crystal White ™, manufactured by Colgate-Palmolive Company) in a proportion of about 1 to 5 volumes of the detergent for each volume of the clay/carbonate combinations. The respecting mixtures were then homogenized and stored until required for use.

EXAMPLE 3

The compositions of Example 2, parts (d) and (e) were used to prepare a water solution of approximately 5 parts of the composition to 100 parts water. The solutions were utilized to effect spray cleaning of the oil-laden interior surfaces of the oil tanker tank compartments of a standard tanker vessel. The solutions removed both new as well as old oil accumulations from the surfaces. After cleaning was completed, the solutions were discharged into a "slop tank," in one instance, and directly into open water in another. The hydrocarbon constituents of the removed petroleum materials were degraded by the *Actinomucor elegans* enzymatic active principles, resulting in a fungus/water solution being all that was discharged into the environment.

While particular embodiments of the invention, and the best mode contemplated by the inventor for carrying out the invention, have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

We claim:

1. A method of effecting degradation of petroleum materials selected from the group consisting of crude petroleum and petroleum products comprising application of *Actinomucor elegans* (Ediam) Benj. & Hasselt, Strain No. TC-405, ATCC 20613, to said petroleum material in an amount effective to degrade said petroleum material.

2. A method of effecting degradation of petroleum materials selected from the group consisting of crude petroleum and petroleum products comprising application of a composition comprising *Actinomucor elegans* (Ediam) Benj. & Hasselt, Strain No. TC-405, ATCC 20613, and a carrier medium to said petroleum material, in an amount effective to degrade said petroleum material.

3. The method of claim 2 wherein said carrier medium contains particulate porcelain clay.

4. The method of claim 2 wherein said carrier medium contains particulate bentonite clay.

5. The method of claims 2, 3 or 4 wherein said carrier medium further comprises particulate sodium carbonate.

6. The method of claims 3 or 4 further comprising the addition of a detergent to said composition prior to application thereof to said petroleum materials.

7. The method of claim 2 further comprising the addition of a detergent to said composition prior to application thereof to said petroleum materials.

8. A method of effecting degradation of petroleum materials selected from the group consisting of crude petroleum and petroleum products, comprising
(a) growing *Actinomucor elegans* (Ediam) Benj. & Hasselt, Strain No. TC-405, ATCC 20613, in a liquid culture medium;
(b) separating and filtering the resulting broth;
(c) adjusting the pH of the filtrate from step (b) to about 4 to 4.5;
(d) adding a carrier medium to said filtrate to absorb an enzymatic active material produced by the fungi;
(e) agitating the carrier medium—filtrate mixture;
(f) separating and recovering the carrier medium from said mixture; and
(g) applying said enzymatic active material-bearing carrier medium to said petroleum material in an amount effective to degrade said petroleum material.

9. The method of claim 8 wherein said culture medium contains glucose and cotton seed hydrolysate.

10. The method of claim 8 wherein said culture medium contains corn starch and cotton seed hydrolysate.

11. The method of claims 9 or 10 wherein said culture medium further contains sodium chloride.

12. The method of claim 8 wherein said carrier medium contains particulate porcelain clay.

13. The method of claim 8 wherein said carrier medium contains particulate bentonite clay.

14. The method of claims 8, 12 or 13 wherein said carrier medium is added to said filtrate in an amount of from about 6 to about 10 grams per liter of said filtrate.

15. The method of claims 12 or 13 wherein said carrier medium further comprises particulate sodium carbonate.

16. The method of claim 14 wherein said carrier medium comprises about 50% by weight particulate sodium carbonate.

17. The method of claim 15 wherein said particulate sodium carbonate is added to the other carrier medium constituents after said constituents are recovered from said filtrate, and said combination is thereafter ground.

18. The method of claim 16 wherein said particulate sodium carbonate is added to the other carrier medium constituents after said constituents are recovered from said filtrate, and said combination is thereafter ground.

19. The method of claims 17 or 18 wherein said ground combination is thereafter air dried under vacuum.

20. The method of claim 8 further comprising the addition of a detergent to said composition prior to application thereof to said petroleum materials.

21. A method of preparing an enzymatic active material for effecting degradation of crude petroleum and petroleum products, comprising
(a) growing *Actinomucor elegans* (Ediam) Benj. & Hasselt, Strain No. TC-405, ATCC 20613, in a liquid culture medium;
(b) harvesting the resulting broth; and
(c) isolating from said broth an enzymatic active material.

22. The method of claim 21 wherein said culture medium contains glucose and cotton seed hydrolysate.

23. The method of claim 21 wherein said culture medium contains corn starch and cotton seed hydrolysate.

24. The method of claim 22 wherein said culture medium further contains sodium chloride.

25. The method of claim 23 wherein said culture medium further contains sodium chloride.

26. A method of preparing a composition for effecting degradation of crude petroleum and petroleum products, comprising
(a) growing *Actinomucor elegans* (Ediam) Benj. & Hasselt, Strain No. TC-405, ATCC 20613, in a liquid culture medium;
(b) separating and filtering the resulting broth;
(c) adjusting the pH of the filtrate from step (b) to about 4 to 4.5;
(d) adding a carrier medium to said filtrate to adsorb an enzymatic active material produced by the fungi;
(e) agitating the carrier medium-filtrate mixture; and
(f) separating and recovering the enzymatic active material-bearing carrier medium composition from said mixture.

27. The method of claim 26 further comprising the addition of a detergent to the enzymatic active material-bearing carrier medium composition.

28. The method of claim 27 wherein said detergent is added to said composition in an amount of about 1 to 5 volumes of said detergent per volume of said composition.

29. The method of claims 26 or 27 wherein said carrier medium contains particulate porcelain clay.

30. The method of claims 26 or 27 wherein said carrier medium contains particulate bentonite clay.

31. The method of claim 29 wherein said carrier medium is added to said filtrate in an amount of from about 6 to about 10 grams per liter of said filtrate.

32. The method of claim 30 wherein said carrier medium is added to said filtrate in an amount of from about 6 to about 10 grams per liter of said filtrate.

33. The method of claim 29 wherein said carrier medium further comprises particulate sodium carbonate.

34. The method of claim 30 wherein said carrier medium further comprises particulate sodium carbonate.

35. The method of claim 33 wherein said particulate sodium carbonate is added to the other carrier medium constituents after said constituents are recovered from said filtrate, and said combination is thereafter ground.

36. The method of claim 34 wherein said particulate sodium carbonate is added to the other carrier medium constituents after said constituents are recovered from said filtrate, and said combination is thereafter ground.

37. The method of claim 35 wherein said ground combination is thereafter air dried under vacuum.

38. The method of claim 36 wherein said ground combination is thereafter air dried under vacuum.

39. The method of claims 26 or 27 wherein said culture medium contains glucose and cotton seed hydrolysate.

40. The method of claims 26 or 27 wherein said culture medium contains corn starch and cotton seed hydrolysate.

41. The enzymatic active material produced by the process of claim 21.

42. The enzymatic active material produced by the process of claim 22.

43. The enzymatic active material produced by the process of claim 23.

44. The enzymatic active material produced by the process of claim 24.

45. The enzymatic active material produced by the process of claim 25.

46. The composition produced by the processes of claims 24, 27 or 28.

47. The composition produced by the process of claim 29.

48. The composition produced by the process of claim 30.

49. The composition produced by the process of claim 31.

50. The composition produced by the process of claim 32.

51. The composition produced by the process of claim 33.

52. The composition produced by the process of claim 34.

53. The composition produced by the process of claim 35.

54. The composition produced by the process of claim 36.

55. The composition produced by the process of claim 37.

56. The composition produced by the process of claim 38.

57. An enzymatic active material which degrades, by emulsification and solubilization, the hydrocarbon constituents of crude petroleum and petroleum materials, produced by *Actinomucor elegans* (Ediam) Benj. & Hasselt, Strain No. TC-405, ATCC 20613.

58. A biologically pure culture of the fungus *Actinomucor elegans* (Ediam) Benj. & Hasselt, Strain No. TC-405, ATCC 20613, said culture being capable of effecting degradation of crude petroleum and petroleum products in an environment.

59. A composition comprising a biologically pure culture of the fungus *Actinomucor elegans* (Ediam) Benj. & Hasselt, Strain No. TC-405, ATCC 20613, said culture being capable of effecting degradation of crude petroleum and petroleum products in an environment, and a carrier medium.

60. A composition for effecting degradation of crude petroleum and petroleum products comprising
(a) an enzymatic active material produced by *Actinomucor elegans* (Ediam) Benj. & Hasselt, Strain No. TC-405, ATCC 20613, and
(b) a carrier medium.

* * * * *